United States Patent
Sorg et al.

(10) Patent No.: US 10,307,281 B2
(45) Date of Patent: Jun. 4, 2019

(54) FOOT PRESSURE APPLICATION METHOD FOR TREATMENT OF IDENTIFIED MEDICAL CONDITIONS, ILLNESSES, AND DISEASES

(71) Applicant: medi USA, L.P., Whitsett, NC (US)

(72) Inventors: Mary Sorg, Waterford, PA (US); Phyllis Kuhn, Girard, PA (US); John Sullivan, Erie, PA (US); Daniel Olson, Erie, PA (US)

(73) Assignee: MEDI USA, L.P., Whitsett, NC (US)

( * ) Notice: Subject to any disclaimer, the term of this patent is extended or adjusted under 35 U.S.C. 154(b) by 713 days.

(21) Appl. No.: 14/791,389

(22) Filed: Jul. 3, 2015

(65) Prior Publication Data

US 2016/0000595 A1 Jan. 7, 2016

Related U.S. Application Data

(60) Provisional application No. 62/021,614, filed on Jul. 7, 2014.

(51) Int. Cl.
*A61F 5/01* (2006.01)

(52) U.S. Cl.
CPC ...................................... *A61F 5/01* (2013.01)

(58) Field of Classification Search
CPC ...... A61H 39/04; A61F 5/0102; A61F 5/0111; A61F 5/0195
See application file for complete search history.

(56) References Cited

U.S. PATENT DOCUMENTS

| | | | |
|---|---|---|---|
| 2005/0049533 A1* | 3/2005 | Beiruti | A43B 7/142 601/118 |
| 2008/0255490 A1 | 10/2008 | Daley | |
| 2009/0024066 A1* | 1/2009 | Sorg | A43B 7/1425 602/27 |
| 2010/0307515 A1* | 12/2010 | Walsh | A61F 13/065 128/894 |
| 2013/0006155 A1* | 1/2013 | Tassin | A61H 1/008 601/27 |
| 2013/0053750 A1* | 2/2013 | Taylor | A61F 13/06 602/75 |
| 2013/0116726 A1* | 5/2013 | Mor | A43B 13/145 606/204 |
| 2013/0218061 A1* | 8/2013 | Cowan | A61F 5/0111 602/28 |
| 2013/0289615 A1* | 10/2013 | Wang | A61H 39/04 606/204 |
| 2014/0309692 A1* | 10/2014 | Mor | A43B 7/144 606/237 |
| 2017/0273851 A1* | 9/2017 | Larmer | A43B 7/146 |

FOREIGN PATENT DOCUMENTS

WO    2013082473 A1    6/2013

* cited by examiner

*Primary Examiner* — Julie A Szpira
(74) *Attorney, Agent, or Firm* — Rimôn, P.C.

(57) ABSTRACT

A method for effecting neuromuscular mechanisms for treatment of specific non-restless leg syndrome, non-restless arms, and non-foot and leg cramps diseases, conditions, and/or illnesses utilizes a device for applying positive pressure to specific areas of the foot. Slight variations to the positioning and/or patient application of the device may be adopted to increase benefits for specific diseases, conditions, or illnesses. Such variations can include frequency or time intervals of use and variations in pressure and positioning of pressure.

36 Claims, 6 Drawing Sheets

FOOT PRESSURE APPLICATION METHOD FOR TREATMENT OF IDENTIFIED MEDICAL CONDITIONS, ILLNESSES, AND DISEASES

CROSS REFERENCE TO RELATED APPLICATION

This application claims the benefit of co-pending U.S. Provisional Patent Application 62/021,614, filed Jul. 7, 2014, which is incorporated herein by reference.

BACKGROUND

The foot is one of the most complicated and sophisticated of all body parts or appendages, and yet its care and maintenance is generally neglected until an affliction or injury occurs, and then the realization supervenes that this is an appendage whose proper functioning is a sine qua non of a healthy, active life. The afflictions, maladies and injuries that can occur to the foot are many. One type of injury that can occur is metatarsalgia—a type of foot pain that occurs in the ball of the foot and that can impede walking and standing. Another affliction is excess pronation—a problem that occurs as part of the process of human gait and which if untreated can lead to progressive bone deformities. A common foot disorder that causes heel spur and other types of plantar facial pain is plantar fasciitis. Relaxing the musculature of the foot commonly treats plantar fasciitis, and this can be accomplished using braces and splints of various designs. It is often the case that the arch of the foot requires support, and thus arch support orthotics can be disposed upon the inner sole of the shoe for building up the shoe thereby supporting the arch of the foot. For providing comfort to the sole of the foot placing a massaging pad on the inner sole of the shoe is a relatively simple and inexpensive expedient.

An affliction of amorphous etiology is restless leg syndrome that can manifest itself in various ways such as by ineluctable creeping sensations and internal itching sensations occurring in the lower extremities. Generally symptoms are more pronounced at the end of the day when the individual is seated or in bed. One way to obtain at least some relief is for the individual to move his or her legs— often for some period of time. However, it is quite common that restless leg syndrome can occur for long periods of time, such as throughout the night, thus frustrating and impeding any possibility of the individual attaining a sound and restful sleep.

Thus, the prior art discloses a range of devices to treat and alleviate the many foot afflictions and ailments.

For example, the Compton patent (U.S. Pat. No. 2,884,719) discloses a device for the relief and prevention of metatarsalgia and includes a support pad comprised of two layers of material with the support pad aligned with and conforming to the inside edge of the shoe so that the weight of the three adjacent metatarsal heads can be redistributed.

The Hoffman patent (U.S. Pat. No. 5,129,395) discloses a shoe insert for preventing excess pronation that is designed to fit the area of void on the plantar side of the human foot and includes a central portion bounded by a convex portion and sloping portions.

The Shanahan patent (U.S. Pat. No. 5,554,107) discloses an elastic foot wrap that is composed of elastic material and includes several toe openings and an ankle opening and which is used for treating plantar fasciitis.

The Chan patent (U.S. Pat. No. 5,735,804) discloses a massaging foot pad for disposition in a shoe or sandal and which includes protrusions arrayed upon a sheet with the protrusions elongated in a horizontal direction and slanted in an orthogonal direction that depress during the downward step and rebound when the foot lifts up off the ground.

The Chtn patent (U.S. Pat. No. 6,141,890) discloses a sole pad unit for supporting the metatarsal bone and massaging the center of the sole of the foot and includes an l-shaped massage block mounted on the sole pad unit and capable of depressing under the pressure of the foot, with the massage block having vents to allow for airflow circulation therethrough.

The Greer Jr. et al. patent (U.S. Pat. No. 6,393,736 B1) discloses an adjustable arch brace orthotic that includes a plurality of adjustable cantilevered extensions that are adjustable by a tensioning means built into the orthotic to vary the arch curve slope and height so that the user's arch can be therapeutically supported.

The Graham patent (U.S. Pat. No. 6,558,339 B1) discloses a foot elevator to alleviate heel and arch pain, and which includes a brace in the form of a semi-elastic bandage that supports the heel and arch of the foot.

The Turtzo patent (U.S. Pat. No. 6,699,209 B2) discloses a foot splint for the treatment of plantar fasciitis that includes a foot plate on which the sole of the foot rests with the proximal and distal portions upwardly angled and securing means that wrap around the foot for attaching the splint thereto.

U.S. Pat. No. 7,753,867 B2 to Sorg discloses a device of the type used in the current invention and a method for using such a device to alleviates the symptoms of restless leg syndrome, restless arms, and foot and leg cramps, in which the device can be unobtrusively worn on the individual's feet for applying pressure over extended periods of time while the individual is non-ambulatory such as when the individual is recumbent or relaxing in a chair. The disclosed apparatus and method targets pressure against muscle groups identified as having a neurological association with the conditions of restless leg syndrome, restless arms, and foot and leg cramps. The entire disclosure of U.S. Pat. No. 7,753,867 B2 is incorporated herein by reference.

SUMMARY

Unexpected results during regulatory trials of the apparatus disclosed in U.S. Pat. No. 7,753,867 B2 demonstrated an observed level of effectiveness in the treatment of restless leg syndrome equal to or exceeding expected levels. Empirically observed benefits to patients using the device during trials also suggested the device could offer benefits in the treatment of conditions in addition to restless leg syndrome, restless arms, and foot and leg cramps. The device is therefore utilized to effect particular neuromuscular mechanisms for the treatment of such additional diseases, conditions, and/or illnesses.

Slight variations to the positioning and/or patient application of the device may be adopted to increase the benefits of using the device for specific diseases, conditions, or illnesses. Such variations can include frequency or time intervals of use, variations in pressure, and positioning of pressure to specific pressure points on the body.

The device of U.S. Pat. No. 7,753,867 B2 is itself a flexible foot relief pad that is wrapped around the individual's foot to alleviate the symptoms associated with restless leg syndrome, restless arms, and foot and leg cramps. The flexible foot relief pad includes a cloth wrapping member that defines a securing portion and a foot engaging or contacting portion with a fold or crease joining the foot engaging portion to the securing portion. The cloth wrapping member is two sided and defines a continuous outer surface and an opposite continuous inner surface. The foot engaging portion of the cloth wrapping member encloses a cavity, and disposed within the cavity is a raised pressure application pad generally of two layers. The first layer is a rectangular base pad that fills the cavity and the second layer is a T-shaped pad that sits on the rectangular pad. The crossbar of the T-shaped pad is parallel with the fold or crease so that when the flexible foot relief pad is wrapped about the individual's foot the crossbar extends along the inner side of the individual's foot and applies specific pressure to the flexor hallucis brevis and the abductor hallucis muscles. In order to secure the flexible foot relief pad on the foot, at least one, and preferably several, VELCRO™ straps extend along the outer surface with a substantial portion of the straps extending beyond the securing portion so that the straps can fully encompass the foot and loop back for attachment to the foot engaging portion thereby securing the flexible pad to the foot. Because the straps incorporate VELCRO™ material, the point of attachment for each strap when the straps are looped back is variable thus allowing the individual to vary or adjust the pressure that is applied to the muscles across the sole of the foot by the multi-layered raised pad, and also to the muscles adjacent the inner side (the big toe side) of the foot. In this configuration, the device is capable of specifically applying pressure to the abductor hallucis and flexor hallucis brevis muscles in the foot. The application of pressure to the desired areas on the sole and inner side of the foot can be adjusted consonant with the severity and duration of the affliction.

BRIEF DESCRIPTION OF THE DRAWINGS

For a more complete understanding and appreciation of this invention, and many of its advantages, reference will be made to the following detailed description taken in conjunction with the accompanying drawings.

DETAILED DESCRIPTION

Referring to the drawings, similar reference numerals are used to designate the same or corresponding parts throughout the several embodiments and figures.

Illustrated in FIGS. 3 through 11 is a device 10 for use with the invention. Device 10 is lightweight, durable, easily washable, and storable, and can be quickly attached to, and detached, from the foot 12 of an individual as needed.

Figure 1:
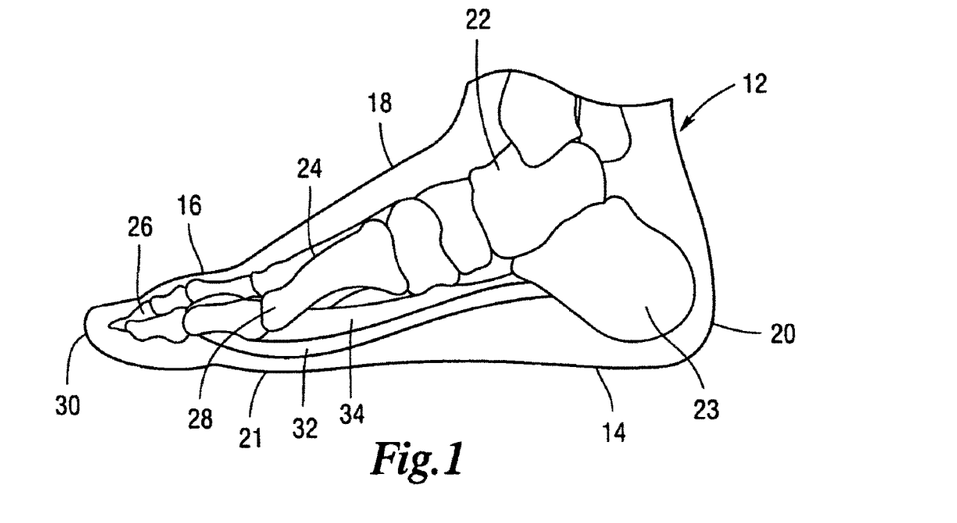
FIG. 1 is a side elevational view illustrating select bones and the muscles of the foot that are to he engaged by a device used in the invention.
Figure 2:
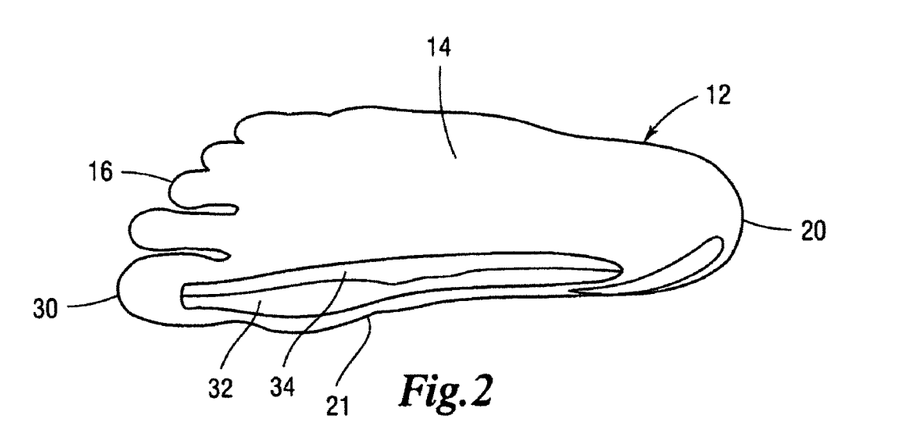
FIG. 2 is a bottom plan view illustrating select bones and the muscles of the foot that are to be engaged by a device used in the invention.

Thus, a representative foot 12 is shown in FIGS. 1 and 2 that include a sole 14, toes 16, a foot upper side 18, a heel 20, and an inner side 21. In addition, for illustrative purposes, prominent bones are shown that include the talus 22, the calcaneus 23, the metatarsals 24, the phalanges 26 and the metatarsal head 28 that is the bony prominence immediately behind the big toe 30. While there are numerous tendons, ligaments, and muscles in foot 12, the muscles of foot 12 to which the present device 10 pertains are the muscle group that includes the medial, plantar and lateral edge of the flexor hallucis brevis muscle 32 and the abductor hallucis muscles 34. The crosspiece or cross bar 68 applies pressure to the side of the abductor hallucis muscles 34 and the flexor hallucis brevis muscles 32; and, the leg or stem 66 applies pressure to the bottom of the flexor hallucis brevis muscle 32 and the abductor hallucis muscles 34. Selective and adjustable application of pressure to these muscles 32 and 34 is applied by device 10 of the present invention.

Figure 9:
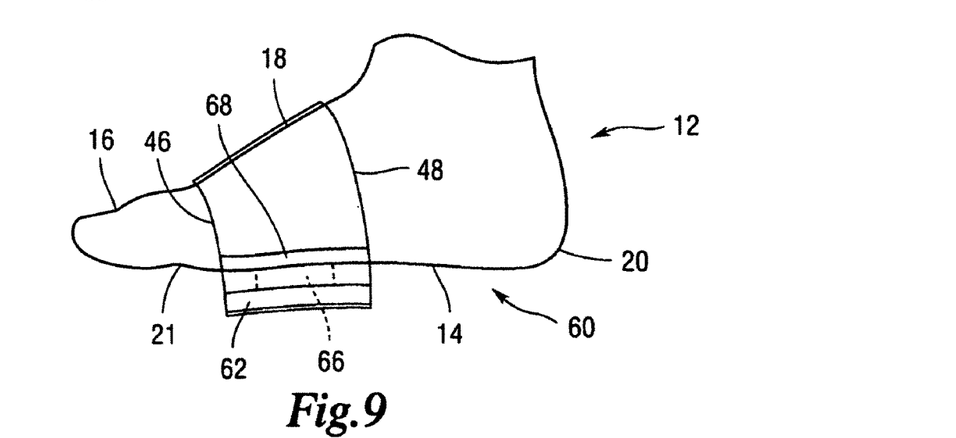
FIG. 9 is a side elevational view of a device used in the invention illustrating the contiguous disposition of the pressure application pad against the sole and/or the inner side of the foot, a right foot is illustrated, the drawing is numbered for use on a right foot.

As shown in FIGS. 3 through 10, device 10 is more particularly a flexible or pliable foot relief pad 36 that is wrapped about and secured to foot 12 as will be hereinafter described. It should be noted that device 10 is to be used when the individual is sitting down or recumbent, and is not to be used when the individual is ambulatory. Foot relief pad 36 includes a cloth wrap or cloth wrapping member 38 that is durable and washable and generally wear resistant. Cloth wrapping member 38 further includes a foot engaging portion 40 that is disposed beneath and contiguous to sole 14 of foot 12 and a foot securing portion 42 that is wrapped about or around upper side 18 of foot 12 for attachment, either directly or indirectly, to foot engaging portion 40. Foot engaging portion 40 and foot securing portion 42 are conjoined by a flexible fold or crease 44 that in effect serves as the demarcation between those portions 40 and 42, and also facilitates the wrapping of foot securing portion 42 about foot 12. In use, device 10 encompasses foot 12 and with foot engaging portion 40 being specifically positioned adjacent and contiguous to the area of sole 14 immediately behind metatarsal head 28 of big toe 30. Thus, cloth wrapping member 38 is further defined by a leading edge 46 that is aligned adjacent to the metatarsal head 28 of big toe 30 and a trailing edge 48 that is disposed toward heel 20 of foot 12 when device 10 is placed on foot 12 as shown in FIG. 9.

Figure 4:
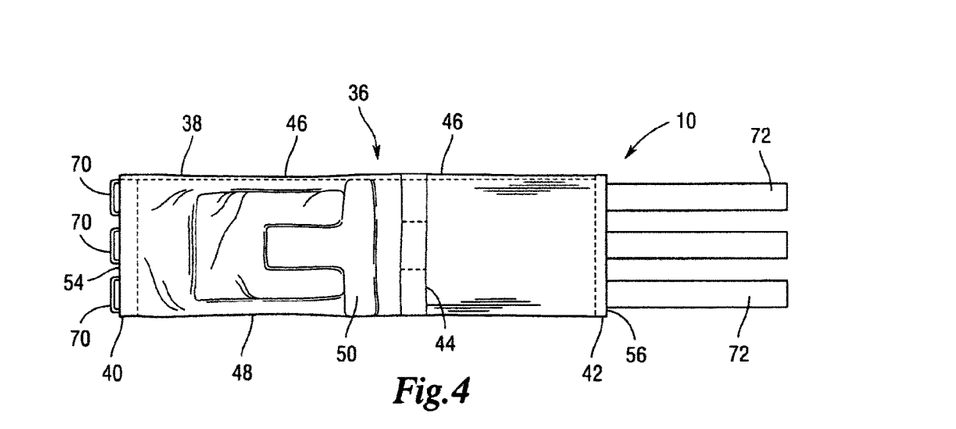
FIG. 4 is a bottom plan view of a device used in the invention.

In FIG. 4, leading edge 46 and trailing edge 48 show device 10 ready for use on a left foot 12.

Figure 10:
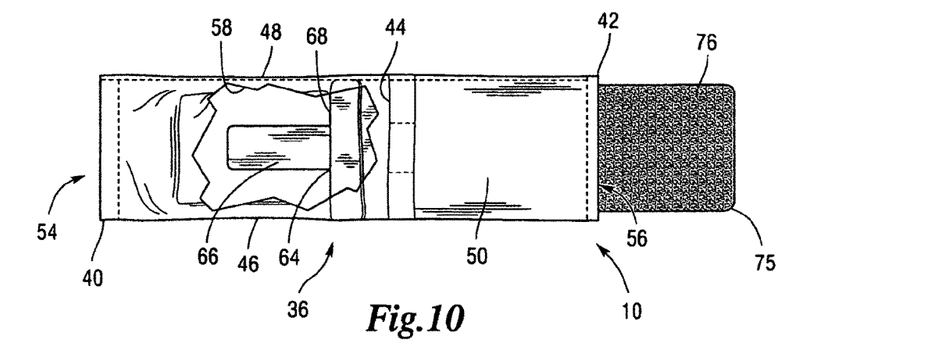
FIG. 10 is a bottom plan view of a device used in the invention illustrating an alternative embodiment for the securement of the device about the foot, the drawing is numbered for use on a left foot.

In FIGS. 9 and 10, leading edge 46 and trailing edge 48 show device 10 ready for use on a right foot 12.

Figure 3:
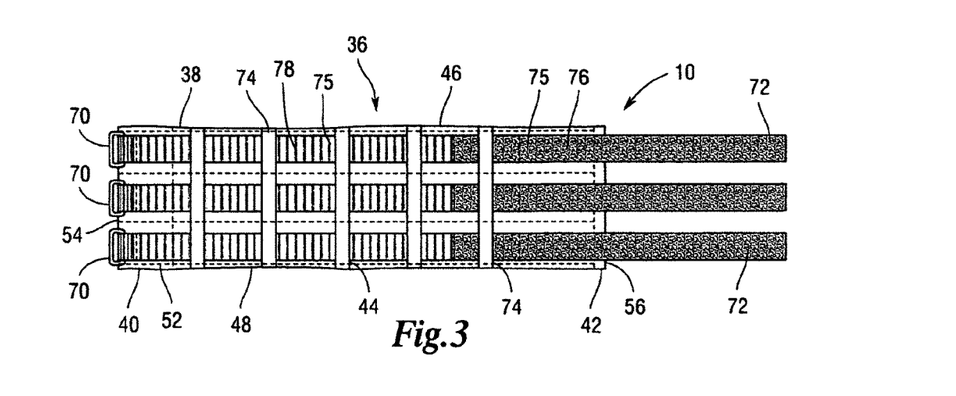
FIG. 3 is a top plan view of a device used in the invention.
Figure 5:
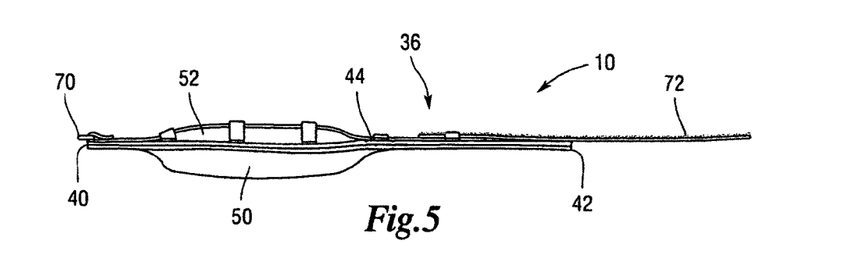
FIG. 5 is a side elevational view of a device used in the invention.
Figure 6:
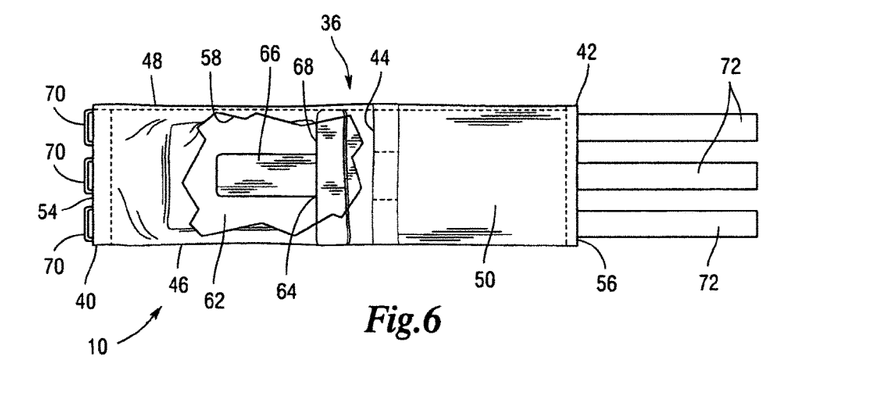
FIG. 6 is a bottom plan view of a device used in the invention, illustrating the foot engaging portion cut away to reveal the disposition of the pressure application pad, the view is numbered for use on a right foot.
Figure 7:
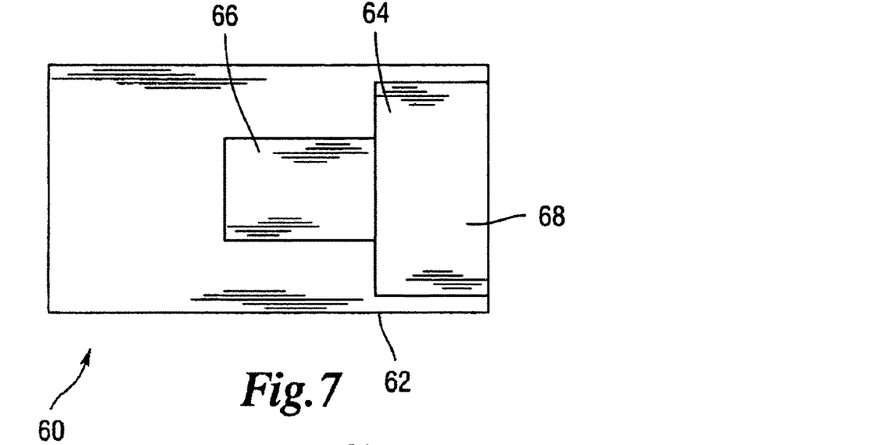
FIG. 7 is a top plan view of a device used in the invention illustrating the layered or upraised structure of the pressure application pad.
Figure 8:
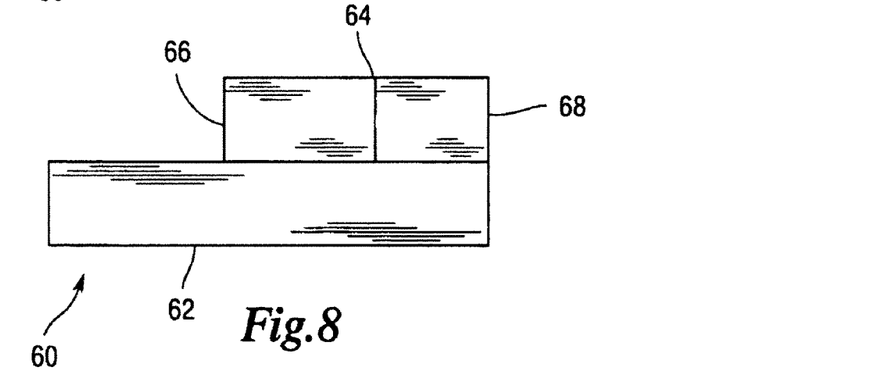
FIG. 8 is a side elevational view a device used in the invention illustrating the layered or upraised structure of the pressure application pad.

In addition, as shown in FIGS. 3 through 5, foot engaging portion 40 and foot securing portion 42 combine to define a continuous inner surface 50 that faces inwardly and contacts foot 12, and an opposite continuous outer surface 52. Moreover, foot engaging portion 40 of foot relief pad 36 includes an attachment edge 54, and foot securing portion 42 includes a wrapping edge 56. When device 10 is placed on foot 12, wrapping edge 56 is brought into proximity with attachment edge 54 so that foot securing portion 42 can be attached to foot engaging portion 40.

As illustrated in FIGS. 6 through 9, foot engaging portion 40 defines a cavity 58; in effect cavity 58 is enclosed between continuous outer surface 52 and continuous inner surface 50. Enclosed or encased within cavity 58 is a multi-layered pressure application pad 60 for providing selective and adjustable pressure to the sole of foot 12. Multi-layered pressure application pad 60 preferably includes two layers; one superposed on the other for creating an upraised pad or pad portion that effectively applies pressure to the above-described muscles 32 and 34 extending along inner side 21 and along sole 14 of foot 12. Thus, pressure application pad 60 includes a rectangular-shaped base pad or portion 62 that fills cavity 58. Rectangular-shaped pad 62 extends transverse within cavity 58 and to sole 14 of foot 1.2 when device 10 is mounted on and secured to foot 12. In addition, superposed on rectangular-shaped pad 62, either as an integral structural element or as a separate structural element, is a T-shaped pad or portion 64 that constitutes the upraised part of pressure application pad 62. T-shaped portion 64 includes a leg or stem 66 that extends along the body of rectangular-shaped pad 62, and also extends transverse to sole 14 of foot 12, and a crosspiece or cross bar 68 that is adjoined to and perpendicular to stem 66 of T-shaped portion 64. When device 10 is to be mounted to foot 12, leading edge 46 of foot relief pad 36 is generally aligned with metatarsal head 28 and crosspiece 68 is aligned with inner side 21 of foot 12 so that crosspiece 68 in particular can apply pressure to those aforementioned muscles 32 and 34 that extend along inner side 21 of foot 12. All the aforedescribed elements of pressure application pad 60 are preferably composed of heavy, high-density foam. While the elements of pressure application pad 60 are composed of high-density foam, pad 60 is somewhat pliable so that pad 60, and especially T-shaped portion 64, can conform to the curvature of inner side 21 of foot 12. In addition, each element of pressure application pad 60—rectangular-shaped portion 62, crosspiece 68 and stem 66—can be separate structural elements; or rectangular-shaped portion 62 and T-shaped portion 64 can be separate structural elements; or, finally, rectangular-shaped base pad 62 and T-shaped portion 64 can be configured from an integral one-piece structure. The primary feature that must be maintained, however, is the upraised configuration of T-shaped portion 64 for abutting and applying pressure to muscles 32, 34 at inner side 21 of foot 12, and leg or stem 66 for abutting and applying pressure to the bottom of muscles 32, 34 of sole 14 of foot 12.

As shown in FIGS. 3 through 6, device 10 includes a securement means for comfortably but securely attaching device 10 on to foot 12 of the individual. More importantly, the securement means is adjustable so that different amounts of pressure on the above-described muscles 32 and 34 can be obtained. The securement means of FIGS. 3 through 6 includes a plurality of eyelets or rings 70 pivotally attached to attachment edge 54 of foot engaging portion 40. Extending from each eyelet 70 and then extending along continuous outer surface 52 of both foot engaging portion 40 and foot securing portion 42 of wrapping member 38 is a flexible strap 72. Flexible straps 72 incorporate separable hook and loop type fasteners 75, such as VELCRO™, material or other suitable fastener, with a portion of each length of each strap 72 comprising first portion 76 of either hook or loop material, and the remaining portion comprising a second portion of the other of hook or loop material 78. Each strap 72 extends past wrapping edge 56 of foot securing portion 42 to insure that straps 72 will encompass foot 12 with enough additional length to provide for their adjustment so that the pressure applied by pressure application pad 60 can be adjusted as desired by the individual. In order to maintain the generally longitudinal extension of straps 72, straps 72 pass beneath a pair of spaced apart retaining members 74 mounted to outer surface 52 and extending transverse to the extension of straps 72. When device 10 is placed on the individual's foot 12 with foot engaging portion 40 located beneath and contiguous with sole 14 of foot 12, straps 72 wrap around foot 12 and are able to loop back upon themselves for securement. Since each strap 72 is securable independent of the other straps 72, each strap 72 can be secured tighter or looser than the other straps 72. This provides for a more selective application of pressure to different areas of sole 14 of foot 12, and thus to the specific muscles 32 and 34 of the aforementioned group of muscles so that one area of sole 14 and inner side 21 can have more pressure applied to it than an adjacent area.

Figure 11:
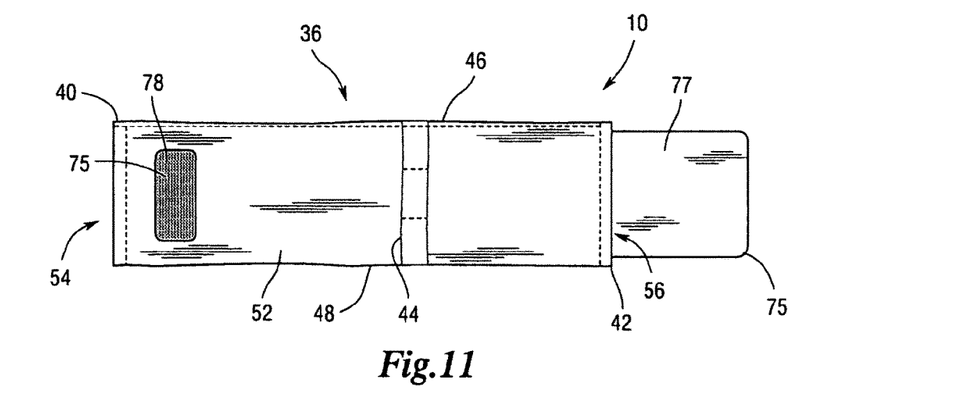
FIG. 11 is a top plan view of a device used in the invention illustrating an alternative embodiment for the securement of the device about the foot.

FIGS. 10 and 11 illustrate an alternative securement means that does not require straps 72 of FIGS. 3 through 6. In FIG. 10 the length of foot securing portion 42 has been extended so that it can fully encompass and overlap part of foot engaging portion 40 for securement thereto. In addition, hook and loop fastener 75 may have first portion 76 of hook and loop fastener 75 comprising either the hook or the loop portion of fastener 75. First portion 76 is attached to inner surface 50 of foot securing portion 42 adjacent wrapping edge 56. Hook and loop fastener 75 may also have second portion 78 of hook and loop fastener 75 comprising the other of the hook or the loop portion of fastener 75. Second portion 78 of hook and loop fastener 75 is attached to outer surface 52 of foot engaging portion 40 adjacent attachment edge 54. The hook and loop fastener material being attached or affixed to securing portion 42 and engaging portion 40 simplifies attachment of the device to the foot. Thus, in order to attach device 10 of FIG. 10 to foot 12, foot securing portion 42 is simply wrapped about foot 12 until it overlaps foot engaging portion 40 whereupon first portion 76 of hook and loop fastener 75 is pressed against second portion 78 of hook and loop fastener 75 thereby securing foot engaging portion 40 to foot securing portion 42 and securing foot relief pad 36 to foot 12. Second portion 78 is secured to outer surface 52 of foot engaging portion 40. First portion 76 has back surface 77 that does not have fasteners thereon.

Figure 12:
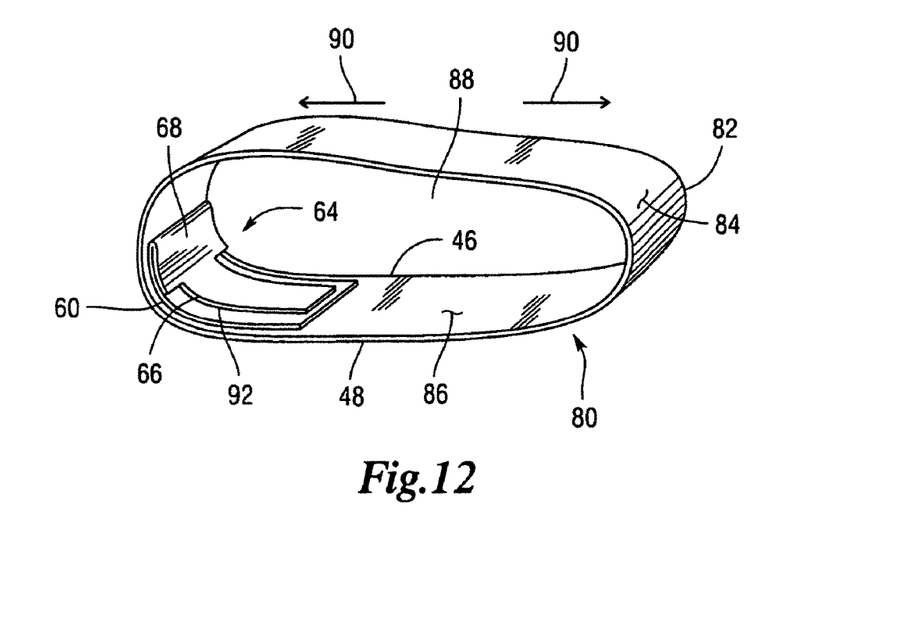
FIG. 12 is a perspective view of an alternative embodiment for a device used in the invention which includes a supporting portion for placement on the foot in the form of an elastic band with the pressure application affixed pad to the inside surface of the band for applying pressure to selected areas on the sole of the foot and/or on the inner side of the foot, the drawing is numbered for use on a right foot.
Figure 13:
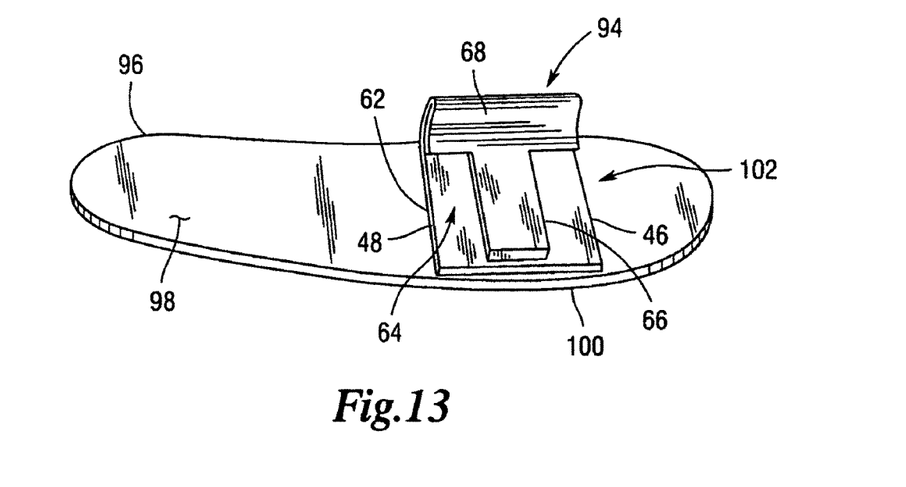
FIG. 13 is a perspective view of a second alternative embodiment for a device used in the invention which includes a shoe insert for placement within a shoe and the pressure application pad affixed thereto so that the pad can apply pressure to selected areas of the sole of the foot and/or on the inner side of the foot, the drawing is numbered for use on a right foot.

Illustrated in FIGS. 12 and 13 are alternative embodiments for device 10 that include pressure application pad 60, but different supporting structures for pad 60. Specifically, FIG. 12 includes a foot pressure positioning means in the form of a lightweight, portable, removable supporting portion 80 that is slipped on to foot 12 and then adjusted so that pad 60 is properly positioned for applying pressure to muscles 32 and 34. Supporting portion 80 includes a flexible elastic band 82, and elastic band 82 defines a continuous external surface 84 and an opposite continuous internal surface 86. When supporting portion 80 is disposed on foot 12 of the individual, elastic band 82 will expand and contract as necessary to fit on to foot 12, and continuous internal surface 86 will abut or be contiguous to foot 12 of the individual. As shown in FIG. 12, supporting portion 80 has a flattened cylindrical shape and further defines a foot aperture 88 through which the individual's foot 12 is inserted for using supporting portion 80. Supporting portion 80 can be adjusted along the length of foot 12, and, in addition, the flattened cylindrical shape allows for the radial slidable adjustment of supporting portion 80 about foot 12. Directional arrows 90 indicate that supporting portion 80 can be rolled in either direction (left/right or medial/lateral) for properly aligning T-shaped portion 64 and stem 66 of pad 60 with the appropriate muscles 32 and 34. Pad 60 is affixed or attached to continuous internal surface 86, and pad 60 serves as the pressure application portion or pressing portion 92 of supporting portion 80.

In use the individual's foot 12 is slipped through foot aperture 88 of elastic band 82, and then elastic band 82 is pushed back on foot 12 so that crosspiece 68 generally aligns with inner side 21 of foot 12, and stem 66 extends transverse to sole 14 of foot 12. Supporting portion 80 is slidably positionable and repositionable upon foot 12; and some radial adjustment of elastic band 82 on foot 12 may be necessary to properly position stem 66 and crosspiece 68 so that stem 66 is aligned for applying pressure to the underside of flexor hallucis brevis muscle 32 and abductor hallucis muscles 34, and crosspiece 68 is aligned for applying pressure to the side of abductor hallucis muscles 34 and flexor hallucis brevis muscles 32. The contraction of elastic band 82 about and against foot 12 causes pressing portion 92, which includes pad 60, stem 66 and crosspiece 68, to continuously press against the aforesaid muscles 32 and 34.

FIG. 13 illustrates a second alternative embodiment for the device shown in FIGS. 1 through 11. Specifically, FIG. 13 illustrates a supporting portion 94 that is a lightweight, portable, removable shoe insert 96 for disposition within a shoe and upon the shoe insole for applying pressure to muscles 32 and 34 as aforedescribed. Shoe insert 96 is preferably rectangular-shaped and includes an upper surface 98 and an opposite lower surface 100. Shoe insert 96 should have some flexibility to allow it to adapt and conform to the particular insole of the shoe. While shoe insert 96 is placed within the shoe and on the insole of the shoe, insert 96 does not have to cover or be commensurate in length and breadth with the insole to apply pressure to foot 12; shoe insert 96 generally needs to be coextensive with that part of sole 14 of foot 12 that includes hallucis brevis muscle 32 and abductor hallucis muscles 34. Affixed or secured to upper surface 98 is pressure application pad 60. Pad 60 is located upon upper surface 98 so that stem 66 and crosspiece 68 can easily be aligned with the corresponding hallucis brevis muscle 32 and abductor hallucis muscles 34. Pad 60, and especially stem 66 and crosspiece 68, specifically serves as pressing portion 102 for supporting portion 94.

Appropriately implemented, the invention allows for the device 10 to be utilized to effect particular neuromuscular mechanisms for the treatment of additional diseases, conditions, and/or illnesses beyond restless leg syndrome, restless arms, and foot and leg cramps.

In a first contemplated example, the device 10 can be utilized for the treatment of conditions such as plantar fasciitis and peripheral neuropathy. The mechanism effective for plantar fasciitis derives from the tension placed by the device 10 on the thick band of foot tissue known as the plantar fascia. When the device 10 constricts the tissue, the typical relaxation that occurs under normal conditions during periods of sleep or rest is prevented. The resulting lack of tension, and the resulting relaxation of tissue fibers that occurs, leads to shortening of the fibers in the fascia, thereby resisting the needed "stretch" of this band when the wearer stands. The constriction on the fibers the device 10 helps prevent their shortening. The device 10 takes advantage of a similar mechanism for peripheral neuropathy. Positive stimuli from the device 10 placed on the peripheral nerve in turn elicits a sensory change causing reduction in painful burning, tingling, pins and needles sensations caused by the condition. It also appears that a blocking of substance P can occur to further reduce symptoms.

It is further contemplated the device 10 can also be utilized for conditions treatable with compression. In some patient situations where edema (swelling) is settled in the forefoot and midfoot, there is no ankle or lower leg edema. The device 10 can be used for forefoot/midfoot compression to milk the edema out of this region.

It is also contemplated the device 10 can be utilized to take advantage of mechanisms involving feedback loops between the central nervous system and the peripheral nervous system (CNS-PNS). Altering this abnormal feedback circuit can potentially down-regulate other abnormal sensory symptoms or motor manifestations. The device 10 can be used to decrease abnormal sensory symptoms such as numbness, pain, and altered sensations as part of the modulation of the sensory components of the feedback loop as previously described. It is further contemplated the device may additionally allow for the down-regulation of abnormal motor manifestations such as cramps, tics, tremors, dystonias, or periodic limb movements.

Analysis of the effects from tested use of the device 10 suggest the device 10 is a significant modulator of the aberrant loop in the CNS-PNS and could apply to other disease states. These additional diseases also have some perpetuation of symptoms with an element of this abnormal feedback loop of the CNS-PNS. The device 10 can be utilized for interruption of this abnormal loop to down-regulate unwanted symptoms involving sensory and/or motor. By direct application of the device 10 as a modulator to this abnormal reflex loop, the device 10 is used to down-regulate unwanted symptomatology from a variety of conditions.

Utilizing mechanisms such as those discussed and described above, it is contemplated some uses of the device 10 would include augmentation and rebound when the discontinuation of dopamine agonists is attempted for some patients. It is further contemplated that with such mechanisms, the device 10 can be used for increasing patient tolerance when doses of dopamine agonist must be increased for medicative effectiveness, where such increased doses would otherwise subject the patient to more side effects. For example, for patients experiencing severe restless leg syndrome and treating the condition with drugs such as MIRAPEX™, the device 10 can be used for a prescribed intervals during a treatment period, such as two weeks, after which the severity of the agonist-induced side effects may be reduced.

It is therefore contemplated the device 10 can be appropriately implemented for use in the treatment of the following non-restless leg syndrome, non-restless arms, and non-foot and leg cramp conditions within the intended scope of the invention:

Anxiety Disorder
Attention Deficit Hyperactivity Disorder
Augmentation and Rebound from Dopamine Agonist Therapy
Back Pain and Chronic Back Pain
Dementia
Depression
Dyskinesia
Dystonia
Fibromyalgia
Foot Pain
Inherited Neuropsychiatric Disorder
Mental Depressive Disorder
Metatarsalgia
Multiple Sclerosis
Muscle Cramp Disorder
Muscular Dystrophy
Nocturnal Foot and Leg Cramps
Neuroma
   Morton's Neuroma
   Plantar Neuroma
   Traumatic Neuroma
Parkinson's Disease
Periodic Limb Movement Disorder
Peripheral Nerve Disorder
Plantar Fasciitis
Obsessive Compulsive Disorder
Radiculopathy
Sacroiliac pain
Tourette Syndrome In addition, it is further contemplated the device can be used for effecting or assisting in Compression Therapy and Muscle Relaxation and also for the treatment of Secondary Restless Leg Syndrome within the intended scope of the invention.

In addition, it is contemplated the device 10 can be utilized according to several application methods incorporating various device application intervals during the course of treatment. All such methods and intervals and all device embodiments shown and described herein are within the intended scope of the current invention and can be appropriately implemented for treatment of any of the above-identified diseases or conditions or be appropriately used for any of the above-identified treatment regimes. The following Example Methods of Application represent only a few of the many such contemplated methods.

EXAMPLE METHOD #1

The patient applies the device 10 by securing a device 10 to each foot and remaining non-ambulatory for three one-hour intervals during the day while the patient is awake. The patient then wears the device again fully during sleep hours. This routine is repeated each day until symptoms subside. It is noted this Example Method #1 would be appropriate for all conditions identified above and would be especially appropriately implemented for the treatment of plantar fasciitis.

EXAMPLE METHOD #2

Pressure is applied to the patient's foot, directed to the abductor hallucis and flexor hallucis brevis muscles to mimic the device 10. After five minutes, the device 10 is placed on the foot for one hour and thereafter removed. After removal of the device 10, additional pressure that mimics the device 10 is applied for an additional five minutes. This method can then be repeated at a later time if symptoms do not subside. It is noted this Example Method #2 would be appropriate for all conditions identified above and would be especially appropriately implemented for the treatment of radiculopathy.

EXAMPLE METHOD #3

The device 10 is worn on both feet at all times the patient is asleep or non-ambulatory, until symptoms subside. The device 10 is in all cases removed after 8 to 10 hours of continuous use, even if the patient remains non-ambulatory.

EXAMPLE METHOD #4

The patient applies the device 10, tightened only to slight pressure, to both feet for one hour and remains non-ambulatory during this interval. At the end of the hour, if symptoms have not yet subsided, the patient tightens the device 10 in small increments for additional one-hour intervals until sufficient pressure has been achieved to relieve symptoms.

EXAMPLE METHOD #5

Same as Example Method #4 above except the patient also wears the device 10 on both feet during sleeping hours and removes the device 10 when the patient wakes up the following morning.

EXAMPLE METHOD #6

The patient applies the device 10 to both feet and remains non-ambulatory only when symptoms occur, with the device 10 being removed promptly upon the subsidence of symptoms. The device 10 is also worn on both feet during all sleeping hours regardless of symptoms.

EXAMPLE METHOD #7

The patient applies the device 10 to both feet whenever the patient is non-ambulatory and as often as possible for a minimum of 30 minutes during each interval, regardless of symptoms. The device 10 is also worn on both feet during all sleeping hours regardless of symptoms.

EXAMPLE METHOD #8

The patient applies the device 10 to both feet for two separate non-ambulatory one-hour intervals during awake hours each day, regardless of symptoms. The device 10 is also worn on both feet during all sleeping hours regardless of symptoms.

EXAMPLE METHOD #9

The patient applies the device 10 to both feet for five to six separate non-ambulatory one-hour intervals during awake hours each day, regardless of symptoms.

EXAMPLE METHOD #10

The patient applies the device 10 according to any of the preceding Examples #1-9, repeated for a period of four to eight days. The device 10 is then unused for a period of two weeks and the prevalence of symptoms is then evaluated.

EXAMPLE METHOD #11

The patient applies the device 10 according to any of the preceding Examples #1-9, repeated for a period of seven to fourteen days. The device 10 is then unused for a period of two weeks and the prevalence of symptoms is then evaluated.

EXAMPLE METHOD #12

The patient applies the device 10 according to any of the preceding Examples #1-11, except the device 10 is applied only to one foot to accommodate other factors precluding the application of the device 10 to either foot.

It should be understood from the foregoing that while particular embodiments of the invention have been shown and described, numerous modifications, alterations and variations are possible and practicable to those skilled in the art without departing from the spirit of the invention or the scope of the appended claims.

The invention claimed is:

1. A method for effecting neuromuscular mechanisms for treatment of specific non-restless leg syndrome, non-restless arms, and non-foot and leg cramps diseases, conditions, and illnesses, the method comprising:
    providing a pressure application pad for providing selective and adjustable pressure to a sole of a foot of an individual, the pressure application pad having a base portion and an upraised portion disposed on the base portion, the upraised portion having a leg and a crosspiece, the leg extending transversely along the sole of the foot, the crosspiece extending about perpendicularly from an end of the leg to extend along the inner side of the foot, the leg being positioned to abut and primarily apply pressure directed to the flexor hallucis brevis muscle at the bottom of the foot, and the crosspiece being positioned to abut and primarily apply pressure directed to the abductor hallucis muscle, the crosspiece being positioned to apply pressure primarily to the inner side of the foot;
    applying pressure with the pressure application pad to both feet of the individual;
    keeping the individual non-ambulatory only when symptoms occur;
    removing the pressure application pad promptly upon the subsidence of symptoms; and
    applying pressure to both feet of the individual with the pressure application pad during all sleeping hours regardless of symptoms;
    the treatment of specific diseases, conditions, and illnesses including the treatment of at least one of Anxiety Disorder, Attention Deficit Hyperactivity Disorder, Augmentation and Rebound from Dopamine Agonist Therapy, Back Pain and Chronic Back Pain, Dementia, Depression, Dyskinesia, Dystonia, Fibromyalgia, Inherited Neuropsychiatric Disorder, Mental Depressive Disorder, Metatarsalgia, Multiple Sclerosis, Muscle Cramp Disorder, Muscular Dystrophy, Nocturnal Foot and Leg Cramps, Neuroma, Morton's Neuroma, Plantar Neuroma, Traumatic Neuroma, Parkinson's Disease, Periodic Limb Movement Disorder, Peripheral Nerve Disorder, Obsessive Compulsive Disorder, Radiculopathy, Sacroiliac Pain, and Tourette Syndrome.

2. The method of claim 1 further comprising:
    applying and securing the pressure application pad to each foot of the individual and maintaining the individual in a non-ambulatory position for three approximately one hour intervals during daytime and while the individual is awake;
    applying and securing the pressure application pad to each foot of the individual while the individual sleeps; and
    continuing to apply the pressure application pad each day until symptoms subside.

3. The method of claim 1 further comprising:
    applying pressure with the pressure application pad to both feet at all times the individual is asleep or non-ambulatory up to about 8 to 10 hours;
    removing the pressure application pad is in all cases after about 8 to 10 hours of continuous use, even if the individual remains non-ambulatory; and
    reapplying pressure with the pressure application pad to both feet if symptoms reappear or until symptoms subside.

4. The method of claim 1 further comprising:
    applying the pressure application pad, tightened only to slight pressure, to both feet of the individual for one hour;
    keeping the individual non-ambulatory while the pressure application pad is tightened only to slight pressure; and
    after one hour, if symptoms have not yet subsided, applying additional small increments of pressure for additional one-hour intervals until sufficient pressure has been added to relieve symptoms.

5. The method of claim 1 further comprising:
    applying the pressure application pad, tightened only to slight pressure, to both feet of the individual for one hour;
    keeping the individual non-ambulatory while the pressure application pad is tightened only to slight pressure;
    after one hour, if symptoms have not yet subsided, applying additional small increments of pressure for additional one-hour intervals until sufficient pressure has been added to relieve symptoms; and
    also applying pressure with the pressure application pad to both feet of the individual during sleeping hours and removing the pressure application pad when the individual wakes up.

6. The method of claim 1 further comprising:
    applying pressure with the pressure application pad to both feet of the individual whenever the individual is non-ambulatory, and as often as possible for a minimum of 30 minute intervals, regardless of symptoms; and
    applying pressure with the pressure application pad to both feet of the individual during all sleeping hours, regardless of symptoms.

7. The method of claim 1 further comprising:
    applying pressure with the pressure application pad to both feet of the individual for two separate, non-ambulatory approximately one-hour intervals during awake hours each day, regardless of symptoms; and
    applying pressure with the pressure application pad to both feet of the individual during all sleeping hours, regardless of symptoms.

8. The method of claim 1 further comprising:
applying pressure with the pressure application pad to both feet of the individual for five to six separate non-ambulatory, approximately one-hour intervals during awake hours each day, regardless of symptoms.

9. The method of claim 1 further comprising applying pressure with the pressure application pad to only one foot of the individual.

10. A method for effecting neuromuscular mechanisms for treatment of specific non-restless leg syndrome, non-restless arms, and non-foot and leg cramps diseases, conditions, and illnesses, the method comprising,:
providing a pressure application pad for providing selective and adjustable pressure to a sole of a foot of an individual, the pressure application pad having a base portion and an upraised portion disposed on the base portion, the upraised portion having a leg and a crosspiece, the leg extending transversely along the sole of the foot, the crosspiece extending about perpendicularly from an end of the leg to extend along the inner side of the foot, the leg being positioned to abut and primarily apply pressure directed to the flexor hallucis brevis muscle at the bottom of the foot, and the crosspiece being positioned to abut and primarily apply pressure directed to the abductor hallucis muscle, the crosspiece being positioned to apply pressure primarily to the inner side of the foot;
applying direct pressure to the abductor hallucis and flexor halluces brevis muscles of the foot of the individual for about five minutes without using the pressure application pad;
applying and securing the pressure application pad to the foot of the individual for about one hour to direct pressure to the abductor hallucis and flexor halluces brevis muscles;
removing the pressure application pad from the foot of the individual;
applying direct pressure to the abductor hallucis and flexor halluces brevis muscles of the foot of the individual for about five additional minutes without using the pressure application pad; and
periodically reapplying and securing the pressure application pad to the foot of the individual whenever symptoms reappear or until symptoms subside;
the treatment of specific diseases, conditions, and illnesses including the treatment of at least one of Anxiety Disorder, Attention Deficit Hyperactivity Disorder, Augmentation and Rebound from Dopamine Agonist therapy, Back Pain and Chronic Back Pain, Dementia, Depression, Dyskinesia, Dystonia, Fibromyalgia, Inherited Neuropsychiatric Disorder, Mental Depressive Disorder, Metatarsalgia, Multiple Sclerosis, Muscle Cramp Disorder, Muscular Dystrophy, Nocturnal Foot and Leg Cramps, Neuroma, Morton's Neuroma, Plantar Neuroma, Traumatic Neuroma, Parkinson's Disease, Periodic Limb Movement Disorder, Peripheral Nerve Disorder, Obsessive Compulsive Disorder, Radiculopathy, Sacroiliac Pain, and Tourette Syndrome.

11. A method for effecting neuromuscular mechanisms for treatment of specific non-restless leg syndrome, non-restless arms, and non-foot and leg cramps diseases, conditions, and illnesses, the method comprising:
providing a pressure application pad for providing selective and adjustable pressure to a sole of a foot of an individual, the pressure application pad having a base portion and an upraised portion disposed on the base portion, the upraised portion having a leg and a crosspiece, the leg extending transversely along the sole of the foot, the crosspiece extending about perpendicularly from an end of the leg to extend along the inner side of the foot, the leg being positioned to abut and primarily apply pressure directed to the flexor hallucis brevis muscle at the bottom of the foot, and the crosspiece positioned to abut and primarily apply pressure directed to the abductor hallucis muscle, the crosspiece being positioned to apply pressure primarily to the inner side of the foot;
applying pressure with the pressure application pad to at least one foot of the individual for repeated, predetermined intervals during a period of about four to eight days;
refraining from applying pressure with the pressure application pad to either foot of the individual for a period of about two weeks; and
evaluating the prevalence of symptoms;
the treatment of specific diseases, conditions, and illnesses including the treatment of at least one of Anxiety Disorder, Attention Deficit Hyperactivity Disorder, Augmentation and Rebound from Dopamine Agonist Therapy, Back Pain and Chronic Back pain, Dementia, Depression, Dyskinesia, Dystonia, fibromyalgia, Inherited Neuropsychiatric Disorder, Mental Depressive Disorder, Metatarsalgia, Multiple Sclerosis, Muscle Cramp Disorder, Muscular Dystrophy, Nocturnal Foot and Leg Cramps, Neuroma, Morton's Neuroma, Plantar Neuroma, Traumatic Neuroma, Parkinson's Disease, Periodic Limb Movement Disorder, Peripheral Nerve Disorder, Obsessive Compulsive Disorder, Radiculopathy, Sacroiliac Pain, and Tourette Syndrome.

12. The method of claim 11,
wherein the period for applying pressure comprises a period of about seven to fourteen days.

13. A method for effecting neuromuscular mechanisms for treatment of specific non-restless leg syndrome, non-restless arms, and non-foot and leg cramps diseases, conditions, and illnesses, the method comprising:
applying pressure with a shoe insert to specific areas of a foot of an individual, the shoe insert having a pressure application pad for providing selective and adjustable pressure to a sole of the foot, the insole having an upper surface and being positionable within a shoe, the pressure application pad being positioned on the upper surface of the insole, the pressure application pad having a base portion and an upraised portion disposed on the base portion, the upraised portion having a leg and a crosspiece, the leg extending transversely along the sole of the foot when the foot is inserted in the shoe, the crosspiece extending about perpendicularly from an end of the leg to extend along the inner side of the foot when the foot is inserted in the shoe, the leg being positioned to abut and primarily apply pressure directed to the flexor hallucis brevis muscle at the bottom of the foot, the crosspiece being positioned to abut and primarily apply pressure directed to the abductor hallucis muscle, and the crosspiece being positioned to apply pressure primarily to the inner side of the foot;
applying pressure with the shoe insert to at least one foot of the individual for repeated, predetermined intervals during a period of about four to eight days;
refraining from applying pressure with the shoe insert to either foot or the individual for a period of about two weeks; and evaluating the prevalence of symptoms:

the treatment of specific diseases, conditions, and illnesses including the treatment of at least one of Anxiety Disorder, Attention Deficit Hyperactivity Disorder, Augmentation and Rebound from Dopamine Agonist Therapy, Back Pain and Chronic Back Pain, Dementia, Depression, Dyskinesia, Dystonia, Fibromyalgia, Inherited Neuropsychiatric Disorder, Mental Depressive Disorder, Metatarsalgia, Multiple Sclerosis, Muscle Cramp Disorder, Muscular Dystrophy, Nocturnal Foot and Leg Cramps, Neuroma, Morton's Neuroma, Plantar Neuroma, Traumatic Neuroma, Parkinson's Disease, Periodic Limb Movement Disorder, Peripheral Nerve Disorder, Obsessive Compulsive Disorder, Radiculopathy, Sacroiliac Pain, and Tourette Syndrome.

14. The method of claim 13 further comprising:

applying and securing the shoe insert to each foot of the individual and maintaining the individual in a non-ambulatory position for three approximately one hour intervals during daytime and while the individual is awake;

applying and securing the shoe insert to each foot of the individual while the individual sleeps; and continuing to apply the shoe insert each day until symptoms subside.

15. The method of claim 13 further comprising:

applying direct pressure to the abductor hallucis and flexor hallucis brevis muscles of the foot of the individual for about five minutes without using the shoe insert;

applying and securing the shoe insert to the foot of the individual for about one hour to direct pressure to the abductor hallucis and flexor hallucis brevis muscles;

removing the shoe insert from the foot of the individual;

applying direct pressure to the abductor hallucis and flexor hallucis brevis muscles of the foot of the individual for about five additional minutes without using the shoe insert; and periodically reapplying and securing the shoe insert to the foot of the individual whenever symptoms reappear or until symptoms subside.

16. The method of claim 13 further comprising:

applying pressure with the shoe insert to both feet at all times the individual is asleep or non-ambulatory up to about 8 to 10 hours;

removing the shoe insert is in all cases after about 8 to 10 hours of continuous use, even if the individual remains non-ambulatory; and reapplying pressure with the shoe insert to both feet if symptoms reappear or until symptoms subside.

17. The method of claim 13 further comprising:

applying the shoe insert, tightened only to slight pressure, to both feet of the individual for one hour;

keeping the individual non-ambulatory while the shoe insert is tightened only to slight pressure; and after one hour, if symptoms have not yet subsided, applying additional small increments of pressure for additional one-hour intervals until sufficient pressure has been added to relieve symptoms.

18. The method of claim 13 further comprising:

applying the shoe insert, tightened only to slight pressure, to both feet of the individual for one hour;

keeping the individual non-ambulatory while the shoe insert is tightened only to slight pressure;

after one hour, if symptoms have not yet subsided, applying additional small increments of pressure for additional one-hour intervals until sufficient pressure has been added to relieve symptoms; and also applying pressure with the shoe insert to both feet of the individual during sleeping hours and removing the shoe insert when the individual wakes up.

19. The method of claim 13 further comprising:

applying pressure with the shoe insert to both feet of the individual;

keeping the individual non-ambulatory only when symptoms occur;

removing the shoe insert promptly upon the subsidence of symptoms; and applying pressure to both feet of the individual with the shoe insert during all sleeping hours regardless of symptoms.

20. The method of claim 13 further comprising:

applying pressure with the shoe insert to both feet of the individual whenever the individual is non-ambulatory, and as often as possible for a minimum of 30 minute intervals, regardless of symptoms; and applying pressure with the shoe insert to both feet of the individual during all sleeping hours, regardless of symptoms.

21. The method of claim 13 further comprising:

applying pressure with the shoe insert to both feet of the individual for two separate, non-ambulatory approximately one-hour intervals during awake hours each day, regardless of symptoms; and applying pressure with the shoe insert to both feet of the individual during all sleeping hours, regardless of symptoms.

22. The method of claim 13 further comprising:

applying pressure with the shoe insert to both feet of the individual for five to six separate non-ambulatory, approximately one-hour intervals during awake hours each day, regardless of symptoms.

23. The method of claim 13, wherein the period for applying pressure comprises a period of about seven to fourteen days.

24. The method of claim 13 further comprising applying pressure with the shoe insert to only one foot of the individual.

25. A method for effecting neuromuscular mechanisms for treatment of specific non-restless leg syndrome, non-restless arms, and non-foot and leg cramps diseases, conditions, and illnesses, the method comprising:

applying pressure with a pressure application pad to specific areas of a foot of an individual, the pressure application pad having an upraised portion having a leg and crosspiece, and providing a wrapping member for encasing the pressure application pad, the wrapping member also having multiple adjustable straps for securing the wrapping member and the pressure application pad, placing and securing the pressure application pad on the foot of an individual with the wrapping member, the leg of the pressure application pad being positioned to abut and primarily apply pressure directed to the flexor hallucis brevis muscle primarily at the bottom of the foot, the crosspiece of the pressure application pad being positioned to abut and primarily apply pressure directed to the abductor hallucis muscle primarily at the inner side of the foot, and adjusting the multiple adjustable straps to selected magnitudes of tightness to adjustably vary the pressure exerted by the leg against the flexor hallucis brevis muscle and by the crosspiece against the abductor hallucis muscle;

applying pressure with the pressure application pad to both feet of the individual;
keeping the individual non-ambulatory only when symptoms occur:
removing the pressure application pad promptly upon the subsidence of symptoms; and
applying pressure to both feet of the individual with the pressure application pad during all sleeping hours regardless of symptoms;
the treatment of specific diseases, conditions, and illnesses including the treatment of at least one of Anxiety Disorder, Attention Deficit Hyperactivity Disorder, Augmentation and Rebound from Dopamine Agonist Therapy, Back Pain and Chronic Back Pain, Dementia, Depression, Dyskinesia, Dystonia, Fibromyalgia, Inherited Neuropsychiatric Disorder, Mental Depressive Disorder, Metatarsalgia, Multiple Sclerosis, Muscle Cramp Disorder, Muscular Dystrophy, Nocturnal Foot and Leg Cramps, Neuroma, Morton's Neuroma, Plantar Neuroma, Traumatic Neuroma, Parkinson's Disease, Periodic Limb Movement Disorder, Peripheral Nerve Disorder, Obsessive Compulsive Disorder, Radiculopathy, Sacroiliac Pain, and Tourette Syndrome.

26. The method of claim 25 further comprising:
applying and securing the pressure application pad to each foot of the individual and maintaining the individual in a non-ambulatory position for three approximately one hour intervals during daytime and while the individual is awake;
applying and securing the pressure application pad to each foot of the individual while the individual sleeps; and
continuing to apply the pressure application pad each day until symptoms subside.

27. The method of claim 25 further comprising:
applying direct pressure to the abductor hallucis and flexor hallucis brevis muscles of the foot of the individual for about five minutes without using the pressure application pad;
applying and securing the pressure application pad to the foot of the individual for about one hour to direct pressure to the abductor hallucis and flexor hallucis brevis muscles;
removing the pressure application pad from the foot of the individual;
applying direct pressure to the abductor hallucis and flexor hallucis brevis muscles of the foot of the individual for about five additional minutes without using the pressure application pad; and
periodically reapplying and securing the pressure application pad to the foot of the individual whenever symptoms reappear or until symptoms subside.

28. The method of claim 25 further comprising:
applying pressure with the pressure application pad to both feet at all times the individual is asleep or non-ambulatory up to about 8 to 10 hours;
removing the pressure application pad is in all cases after about 8 to 10 hours of continuous use, even if the individual remains non-ambulatory; and
reapplying pressure with the pressure application pad to both feet if symptoms reappear or until symptoms subside.

29. The method of claim 25 further comprising:
applying the pressure application pad, tightened only to slight pressure, to both feet of the individual for one hour;
keeping the individual non-ambulatory while the pressure application pad is tightened only to slight pressure; and
after one hour, if symptoms have not yet subsided, applying additional small increments of pressure for additional one-hour intervals until sufficient pressure has been added to relieve symptoms.

30. The method of claim 25 further comprising:
applying the pressure application pad, tightened only to slight pressure, to both feet of the individual for one hour;
keeping the individual non-ambulatory while the pressure application pad is tightened only to slight pressure;
after one hour, if symptoms have not yet subsided, applying additional small increments of pressure for additional one-hour intervals until sufficient pressure has been added to relieve symptoms; and
also applying pressure with the pressure application pad to both feet of the individual during sleeping hours and removing the pressure application pad when the individual wakes up.

31. The method of claim 25 further comprising:
applying pressure with the pressure application pad to both feet of the individual whenever the individual is non-ambulatory, and as often as possible for a minimum of 30 minute intervals, regardless of symptoms; and
applying pressure with the pressure application pad to both feet of the individual during all sleeping hours, regardless of symptoms.

32. The method of claim 25 further comprising:
applying pressure with the pressure application pad to both feet of the individual for two separate, non-ambulatory approximately one-hour intervals during awake hours each day, regardless of symptoms; and
applying pressure with the pressure application pad to both feet of the individual during all sleeping hours, regardless of symptoms.

33. The method of claim 25 further comprising:
applying pressure with the pressure application pad to both feet of the individual for five to six separate non-ambulatory, approximately one-hour intervals during awake hours each day, regardless of symptoms.

34. The method of claim 25 further comprising applying pressure with the pressure application pad to only one foot of the individual.

35. A method for effecting neuromuscular mechanisms for treatment of specific non-restless leg syndrome, non-restless arms, and non-foot and leg cramps diseases, conditions, and illnesses, the method comprising:
applying pressure with a pressure application pad to specific areas of foot of an individual, the pressure application pad having an upraised portion having a leg and crosspiece, and providing a wrapping member for encasing the pressure application pad, the wrapping member also having multiple adjustable straps for securing the wrapping member and the pressure application pad, placing and securing the pressure application pad on the foot of an individual with the wrapping member, the leg of the pressure application pad being positioned to abut and primarily apply pressure directed to the flexor hallucis brevis muscle primarily at the bottom of the foot, the crosspiece of he pressure application pad being positioned to abut and primarily apply pressure directed to the abductor hallucis muscle primarily at the inner side of the foot, and adjusting the multiple adjustable straps to selected magnitudes of tightness to adjustably vary the pressure exerted by the leg against the flexor hallucis brevis muscle and by the crosspiece against the abductor hallucis muscle;

applying pressure with the pressure application pad to at least one foot of the individual for repeated, predetermined intervals during a period of about four to eight days;

refraining from applying pressure with the pressure application pad to either foot of the individual for a period of about two weeks; and evaluating the prevalence of symptoms;

the treatment of specific diseases, conditions, and illnesses including the treatment of least one of Anxiety Disorder, Attention Deficit Hyperactivity Disorder, Augmentation and Rebound from Dopamine Agonist Therapy, Back Pain and Chronic Back Pain, Dementia, Depression, Dyskinesia, Dystonia, Fibromyalgia, Inherited Neuropsychiatric Disorder, Mental Depressive Disorder, Metatarsalgia, Multiple Sclerosis, Muscle Cramp Disorder, Muscular Dystrophy, Nocturnal Foot and Leg Cramps, Neuroma, Morton's Neuroma, Plantar Neuroma, Traumatic Neuroma, Parkinson's Disease, Periodic Limb Movement Disorder, Peripheral Nerve Disorder, Obsessive Compulsive Disorder, Radiculopathy, Sacroiliac Pain, and Tourette Syndrome.

36. The method of claim 35, wherein the period for applying pressure comprises a period of about seven to fourteen days.

* * * * *